United States Patent
Stillman

(10) Patent No.: US 10,420,887 B2
(45) Date of Patent: Sep. 24, 2019

(54) SYRINGE INJECTION AID

(71) Applicant: Andrew H. Stillman, Woodland, MN (US)

(72) Inventor: Ralph Stillman, Excelsior, MN (US)

(73) Assignee: Sara Chelstrom, Maple Plain, MN (US)

( * ) Notice: Subject to any disclaimer, the term of this patent is extended or adjusted under 35 U.S.C. 154(b) by 144 days.

(21) Appl. No.: 15/594,983

(22) Filed: May 15, 2017

(65) Prior Publication Data

US 2017/0246389 A1    Aug. 31, 2017

Related U.S. Application Data

(63) Continuation-in-part of application No. 14/864,595, filed on Sep. 24, 2015, now abandoned.

(60) Provisional application No. 62/054,596, filed on Sep. 24, 2014.

(51) Int. Cl.
| | |
|---|---|
| *A61M 5/178* | (2006.01) |
| *A61M 5/46* | (2006.01) |
| *A61J 1/20* | (2006.01) |
| *A61M 5/28* | (2006.01) |
| *A61M 5/315* | (2006.01) |
| *A61M 5/32* | (2006.01) |
| *A61M 5/24* | (2006.01) |

(52) U.S. Cl.
CPC .......... *A61M 5/1782* (2013.01); *A61J 1/2096* (2013.01); *A61M 5/46* (2013.01); *A61J 1/2065* (2015.05); *A61M 5/28* (2013.01); *A61M 5/31551* (2013.01); *A61M 5/31591* (2013.01); *A61M 5/3202* (2013.01); *A61M 5/3243* (2013.01); *A61M 2005/2414* (2013.01)

(58) Field of Classification Search
CPC .................. A61M 5/1782; A61M 5/46; A61M 2005/2414; A61M 5/28; A61J 1/2096
See application file for complete search history.

(56) References Cited

U.S. PATENT DOCUMENTS

| | | | |
|---|---|---|---|
| 5,226,895 | A | 7/1993 | Harris |
| 5,733,261 | A | 3/1998 | Obong |
| 6,171,284 | B1 | 1/2001 | Kao et al. |
| 6,270,479 | B1 | 8/2001 | Bergens et al. |
| 7,470,259 | B2 | 12/2008 | Hoyle, Jr. |
| D651,309 | S | 12/2011 | Rowe et al. |
| RE43,834 | E | 11/2012 | Steenfeldt-Jensen et al. |
| 2006/0189938 | A1 | 8/2006 | Hommann et al. |
| 2011/0172602 | A1 | 7/2011 | Eaton |
| 2011/0196310 | A1 | 8/2011 | Cronenberg |

(Continued)

*Primary Examiner* — Bradley J Osinski
(74) *Attorney, Agent, or Firm* — Hollingsworth Davis, LLC

(57) ABSTRACT

An apparatus comprises a body having an opening at a first end of the body. A plunger control grip is slidably coupled to a portion of the body circumference and configured to couple to a syringe plunger. The apparatus further comprises a cover pivotably coupled to the first end of the body, wherein in an open position the cover exposes a cavity configured to receive a syringe. A locking mechanism is pivotally secured to the cover, wherein the locking mechanism is configured to prevent forward movement of the plunger control grip when in a locked position and to enable forward movement of the plunger control grip when in an unlocked position. The unlocked position is activated by external contact with the locking mechanism and forward movement is in the direction toward the first end of the body.

20 Claims, 9 Drawing Sheets

(56) References Cited

U.S. PATENT DOCUMENTS

2012/0184918 A1    7/2012   Bostrom
2014/0039407 A1    2/2014   Schoonmaker
2016/0082201 A1    3/2016   Stillman

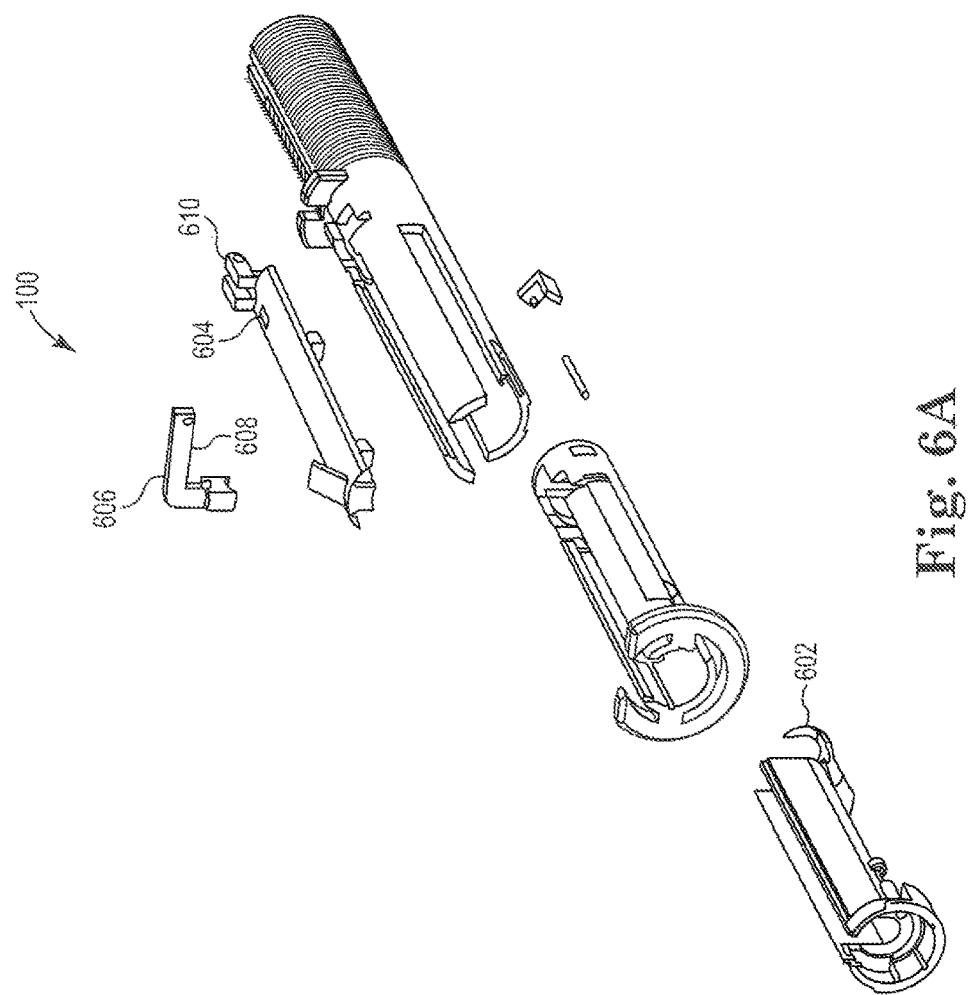

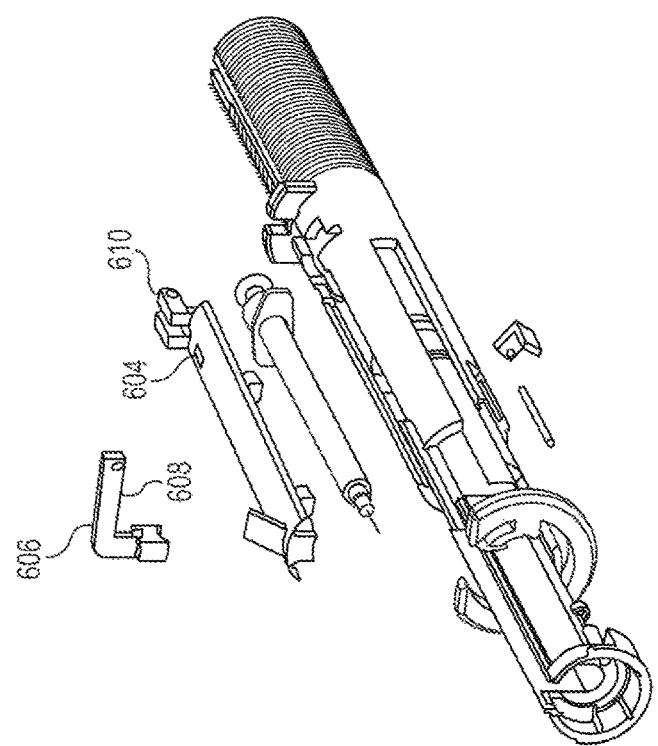

SYRINGE INJECTION AID

RELATED APPLICATIONS

This application is a continuation-in-part of U.S. Ser. No. 14/864,595, filed Sep. 24, 2015, which is incorporated herein by reference in its entirety. This application also claims the benefit of provisional patent application U.S. Ser. No. 62/054,596 filed on Sep. 24, 2014, to which priority is claimed pursuant to 35 U.S.C. § 119(e) and which is incorporated herein by reference in its entirety.

FIELD OF THE DISCLOSURE

The present disclosure relates to injection devices and, more particularly, to an injection aid device configured to interact with a syringe.

BACKGROUND

Numerous individuals are faced daily with the task of injecting themselves or others with medication. A typical injection scene finds the individual with a two-handed task of holding a vial of medication in one hand while trying to align a syringe, held in the other hand, with the vial. Once the needle of the syringe is injected into the vial, the individual must hold the syringe and vial in position while drawing back the plunger of the syringe to withdraw a specific dosage amount into the syringe. The individual must then position the syringe at a desired injection site then maintain that position and needle depth while simultaneously depressing the syringe plunger to deliver the medication. The multi-step process of delivering an injection requires significant manual dexterity. For those individuals lacking manual dexterity, the process can become very difficult and can present the individual with frustration and even safety issues due to, for example, the dropping and contamination of the syringe, unintended jabs with the needle, and, unfortunately, even the failure to deliver a medication that is needed to maintain health. As such, there is a need for an injection aid that can ensure confident and successful delivery of an injection time after time.

SUMMARY

A syringe injection aid includes a body, a syringe-interfacing plunger slidably contained within the body, and a locking mechanism. The body has a lower opening defined by an actuation collar. The locking mechanism is pivotally secured to the body and has a locked and unlocked position. The locking mechanism is configured to prevent forward movement of the syringe-interfacing plunger when in a locked position and is configured to enable forward movement, i.e. towards an injection site, of the syringe-interfacing plunger when in an unlocked position. The unlocked position is activated by external contact with the activation collar.

A syringe injection aid includes a containment means, a syringe-interfacing means slidably contained within the containment means and a locking means. The syringe-interfacing means is for interfacing with a syringe having a needle. The locking means is pivotally secured to the containment means and has a locked and unlocked position. The locking means is for preventing forward movement of the syringe-interfacing means when in a locked position and for enabling forward movement, i.e. towards an injection site, of the syringe-interfacing means when in an unlocked position. The actuation means is for unlocking the locking means upon being externally contacted.

A syringe injection aid includes an outer shell, a plunger, and a tube support. The plunger is slidably contained by the outer shell and is configured to interface with a syringe; the plunger has an injection delivery position. The tube support is coupled to the outer shell and includes a pivotable locking arm and an actuation collar. Upon external actuation of the actuation collar the locking arm is moved into an unlocked position enabling the plunger to slide past the locking arm to the injection delivery position. Upon retreat from the injection delivery position, the plunger causes the locking arm to move into a locked position.

An embodiment of a syringe injection aid includes a body, a plunger, and a mechanism. The body is configured to substantially confine a syringe having a syringe plunger, a syringe body, and a needle. The plunger is substantially, slidably contained within the body. The mechanism is configured to interface with a surface of the plunger. Upon the mechanism engaging the surface of the plunger, the mechanism also engages the syringe body to move the needle of the syringe a distance beyond the confines of the body. Upon the mechanism subsequently disengaging the surface of the plunger, the plunger engages the syringe plunger to move the syringe plunger toward the syringe body while maintaining the distance of the needle from the body.

The mechanism may comprise a ratchet for engaging an interior, slatted surface of the plunger. The plunger may include a graspable element that is exterior of the body. The plunger may additionally be configured to activate a position lock and the body may additionally be configured to deactivate the position lock upon the body contacting the neck of a medication vial. The plunger may additionally be configured to draw the syringe plunger away from the syringe body. The body may additionally be configured to establish a dosage for the syringe.

Additional embodiments are directed to an apparatus comprising a body having an opening at a first end of the body. A plunger control grip is slidably coupled to a portion of the body circumference and is configured to couple to a syringe plunger. The apparatus also includes a cover pivotably coupled to the first end of the body, wherein in an open position the cover exposes a cavity configured to receive a syringe. A locking mechanism is pivotally secured to the cover, wherein the locking mechanism is configured to prevent forward movement of the plunger control grip when in a locked position and to enable forward movement of the plunger control grip when in an unlocked position. The unlocked position is activated by external contact with the locking mechanism, and forward movement is in the direction toward the first end of the body.

Other embodiments are directed to an apparatus comprising a tubular body having an opening at a first end of the tubular body and a plunger control grip slidably coupled to and encircling a portion of the tubular body circumference, where the plunger control grip is configured to couple to a syringe plunger. A cover is pivotably coupled to the tubular body, wherein in an open position the cover exposes a cavity configured to receive a syringe. A locking mechanism is pivotally secured to the cover, wherein the locking mechanism is configured to prevent forward movement of the plunger control grip when in a locked position and to enable forward movement of the plunger control grip when in an unlocked position. Forward movement is in the direction toward the first end of the tubular body.

Further embodiments are directed to an apparatus comprising a body having an opening at a first end of the body and the body being configured to receive and substantially confine a syringe having a syringe plunger, a syringe body, and a needle. A plunger control grip is slidably coupled to a portion of the body circumference and configured to couple to the syringe plunger and the syringe body. A cover is pivotably coupled to the first end of the body, wherein in an open position the cover exposes a cavity configured to receive the syringe. A locking mechanism is pivotally secured to the cover, wherein the locking mechanism is configured to prevent forward movement of the plunger control grip when in a locked position and to enable forward movement of the plunger control grip when in an unlocked position, wherein forward movement of the plunger control grip is in the direction toward the first end of the body and engages the syringe body to move the needle a distance beyond the confines of the body.

The above summary is not intended to describe each embodiment or every implementation. A more complete understanding will become apparent and appreciated by referring to the following detailed description and claims in conjunction with the accompanying drawings.

BRIEF DESCRIPTION OF THE DRAWINGS

FIG. 6A is an exploded assembly view of a syringe injection according to various embodiments.

FIG. 6B is a substantially assembled syringe injection aid of FIG. 6A relative to a syringe according to various embodiments.

DETAILED DESCRIPTION

Figure 1:
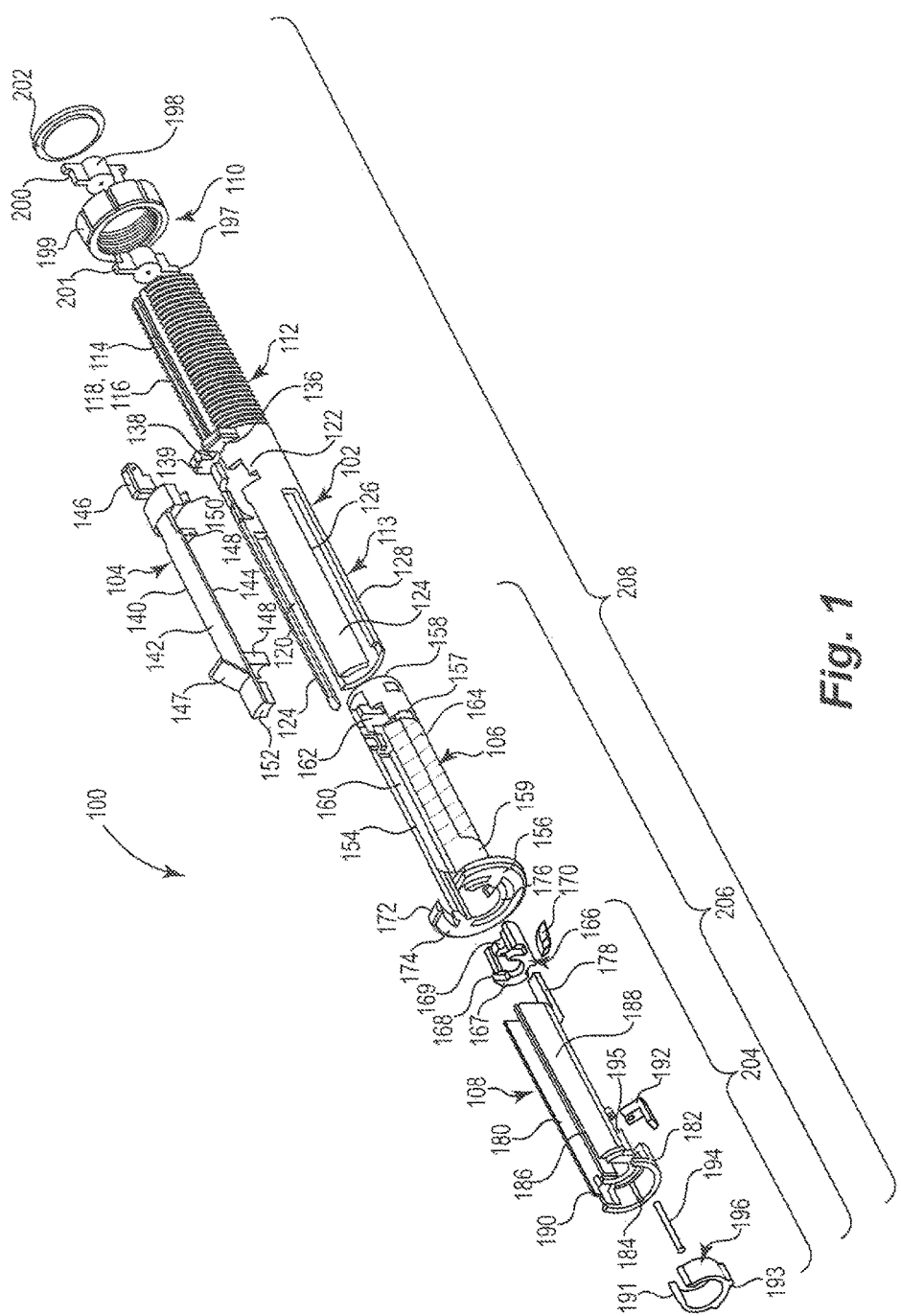
FIG. 1 is an exploded assembly view of a syringe injection aid according to various embodiments.
Figure 3:
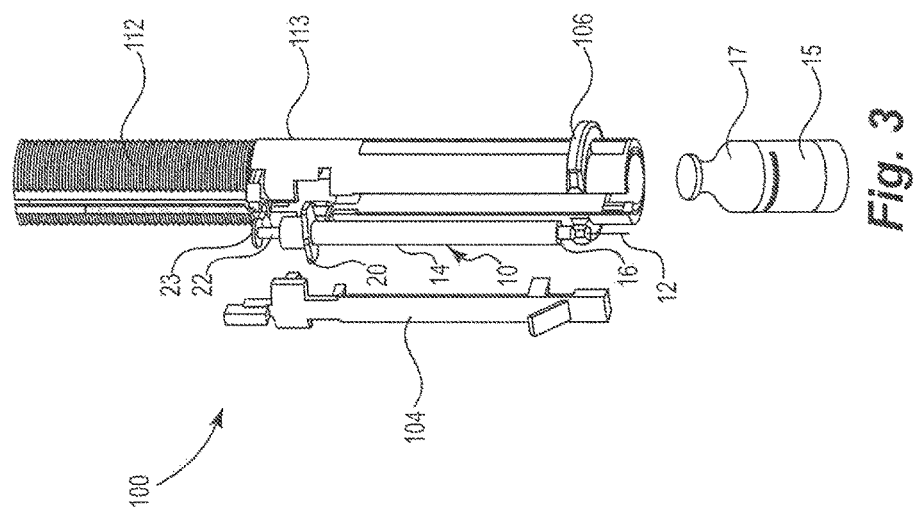
FIG. 3 is a substantially assembled syringe injection aid relative to a syringe according to various embodiments.
Figure 2:
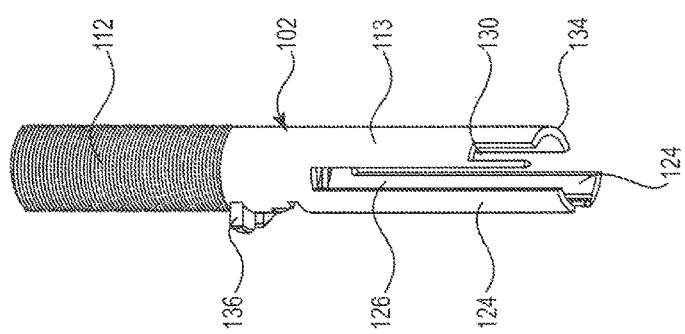
FIG. 2 is side perspective of the outer shell of FIG. 1.
Figure 4:
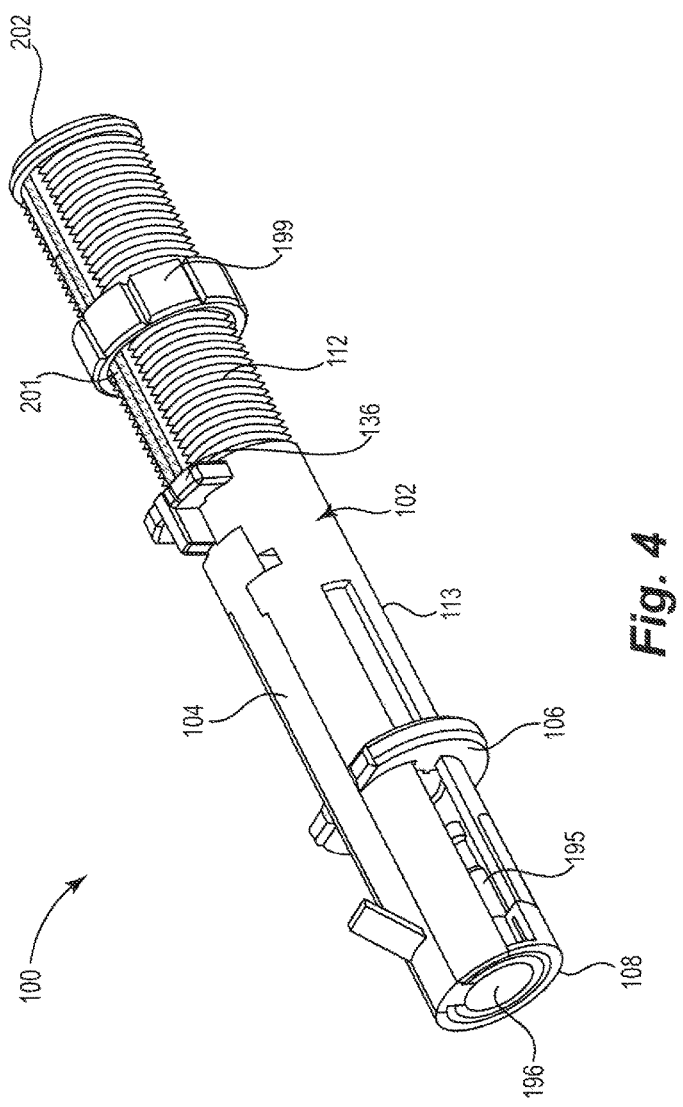
FIG. 4 is a fully assembled syringe injection aid according to various embodiments.

A syringe injection aid 100 of the present disclosure is illustrated in FIGS. 1-4 and is configured to interface with a standard syringe 10. The standard syringe, shown in FIG. 3, includes a needle 12, a syringe body 14 presenting a lower neck 16, side handles 20, and a syringe plunger 22 with a plunger cap 23. In utilizing the syringe injection aid 100 of the present disclosure, the user is provided with a multi-use device that enables one-handed injection as well as needle protection and needle depth control.

As shown, the syringe injection aid 100 generally comprises an outer shell 102, a side cap 104, a plunger 106, a tube support 108 and a gauge 110. The outer shell 102, most clearly seen in FIGS. 1 and 2, comprises a tubular configuration having a threaded upper portion 112 and a multi-slotted lower portion 113. The threaded upper portion 112 includes a centrally positioned slot 114 extending the length thereof. An inner lip 116 of the slot 114 is provided with a notched surface 118 with movement along each notch indicating a specific dosage. The lower portion 113 of the outer shell 102 is configured to receive the plunger 106 and accommodate portions of the tube support 108. Specifically, the lower portion 113 includes a centrally positioned slot 120, substantially extending the length thereof, that has been configured to accept the standard syringe 10 and thus includes a widened opening 122 designed to accommodate the side handles 20 and the plunger 22 of the syringe 10. The slot 120 is defined to either side by legs 124. The lower portion 113 further includes side slots 126 that are defined on one side by legs 124 and on the other side by rear portion 128. The rear portion 128 incorporates an indent 134 and a latch slot 130 into which a latch 192 is secureably and pivotally positioned The outer shell 102 is further defined by a side cap positioner 136 that extends outward from the lower portion 113 and is positioned intermediate the upper portion 112 and the lower portion 113. The side cap positioner 136 is defined by a central opening 138 that establishes first and second side portions 139 of the side cap positioner 136.

The side cap 104 is configured to interface with slot 120 of the lower portion 113 of the outer shell 102 and to interface with a syringe 10 held within lower portion 113. As such, the side cap 104 comprises an elongate body portion 140 having an exterior surface 142 and an interior surface 144. The exterior surface 142 is provided with a raised positioning tab 146 and a removal tab 147. The raised positioning tab 146 serves to centrally position the side cap 104 within the slot 120 and provides a snap fit to the first and second side portions 139 of the side cap positioner 136. The removal tab 147 extends angularly away from the exterior surface 142 and functions as a graspable lever by which to pivot or remove the side cap from the outer shell 102. The interior surface 144 of the side cap 104 is provided with upper and lower retention tabs 148 to assist in maintaining the position of an underlying syringe 10; the retention tabs 148 present curved forward faces to accommodate the curvature of the syringe body 14. The interior surface 144 additionally includes a ratchet stop 150. The interior surface 144 further includes a lower stabilizer 152 to stabilize the side cap 104 and assist in maintaining the side cap 104 in the slot 120; the lower stabilizer 152 also blocks access to the needle 12 of the syringe 10 when the needle 12 is in a retracted position. As such, the needle 12 is essentially confined within the syringe injection aid 100.

The plunger 106 is configured to be slidably received by the outer shell 102. The plunger 106 includes an elongate, tubular stem portion 154, an engagement flange 156, and a top cap 158. The tubular stem portion 154 includes side slot 157 which allows syringe 10 to slide by without engaging and a latch slot 159. A central slot 160, extending from the top cap 158 through the engagement flange 156, is configured to be substantially aligned with the slot 120 of the outer shell 102. The interior of the plunger 106 is provided with a slotted stop 162 proximate the top cap 158 and a slatted, interior rear surface 164, illustrated with hidden, dashed lines, to provide an interfacing surface for a ratchet 166. The ratchet 166 includes a ratchet body 168 and a catch 170, for example, a spring steel catch, ratchet arms 167, and an upper neck portion 169. The ratchet 166 is configured to accommodate the tubular configuration of the plunger 106. When the plunger 106 is received within the outer shell 102, the engagement flange 156 operates to engage the outer shell 102. In doing so, the engagement flange 156 utilizes a pair of outer arms 172, which are configured to slide along the legs 124 of outer shell 102, and a pair of intermediate arms 174, which slidably engage side slots 126 of the outer shell 102 to maintain the desired operational orientation of the plunger 106 relative to the outer shell 102. The engagement flange 156 additionally includes a curved receiving slot 176 that extends between intermediate arms 174.

The tube support 108 is configured to interface with the slidable plunger 106 and with the outer shell 102. The tube support 108 includes a centrally positioned upper tab 178, which is configured to engage the ratchet 166, a central body portion 180, and a lower tab 182 having a notched, arcuate face 184. The central body portion 180 includes an elongate central cavity 186 substantially aligned with slots 120 and 160 and elongate side walls 188 over which the tubular stem portion 154 of the plunger 106 may slide. The central body portion 180 further includes a pair of lower arm extensions 190. The tube support 108 is additionally configured to accommodate a latch trigger 194 through use of a latch/trigger receptor 195, explained further below, as well as a tube support insert 196 having alignment tabs 193 and upper engagement edges 191.

The gauge 110 includes a lower stop portion 197, an upper stop portion 198, and an adjustment ring 199. The lower stop portion 197 and upper stop portion 198 each incorporate a side wing 200 configuration with the side wing 200 of the lower stop portion 197 incorporating an indicator 201 that extends through slot 114 proximate notched surface 118 to indicate a selected dosage. The lower stop portion 197 and upper stop portion 198 are positioned to either side of the adjustment ring 199 and are connected there through by appropriate connection device, e.g., a screw. An end cap 202 may be provided to seal off the upper end of the outer shell 102.

To assemble the syringe injection aid 100, it is generally desirable to first complete the support tube assembly 204. However, it should be noted that, any assembly sequence resulting in the desired finished product is contemplated by the present disclosure. To begin the support tube assembly 204, the latch/trigger receptor 195 is fitted with a spring (not shown) and the latch trigger 194, for example, an elongate pin, is provided at each side of the spring. The tube support insert 196 is then slid into the tube support 108. Note that the alignment tabs 193 of the tube support insert 196 are accommodated by the notched arcuate face 184 of the lower tab 182 of the tube support 108 and the upper engagement edges 191 of the tube support insert 196 actively engage the pair of lower arm extensions 190 of the tube support 108. The tube support assembly 204 is now complete.

In continuing the assembly of the syringe injection aid 100, the tube support assembly 204 is incorporated into the plunger 106 to produce the plunger assembly 206. First, the ratchet 166, with the catch 170 already secured to the ratchet body 168, may be placed within the tubular stem portion 154 proximate slotted stop 162 of the plunger 106. Then central body portion 180 and upper tab 178 of the tube support are inserted into the tubular stem portion 154 of the plunger 106. As the tube support 108 is slid into the plunger 106, the lower tab 182 of the tube support 108 engages the curved receiving slot 176 of the engagement flange 156 and is slid there through until the arcuate face 184 of the lower tab 182 is flush with the engagement flange 156. The plunger assembly 206 is now complete.

Further assembly of the syringe injection aid 100 provides for incorporating the plunger assembly 206 into the outer shell 102 to establish the outer shell assembly 208. First, the latch 192 is pivotally secured within the latch slot 130. Then, the plunger assembly 206 is slid into the multi-slotted lower portion 113 of the outer shell 102. In so doing, the centrally positioned slot 120 of the lower portion 113 of the outer shell 120 is substantially aligned with the central slot 160 of the plunger 106, which is substantially aligned with the elongate central cavity 186 of the tube support 108. Further the intermediate arms 174 of the plunger 106 are engaged with the side slots 126 of the outer shell 102, the outer arms 172 of the plunger 106 are slidably positioned over the legs 124 of the outer shell 102. The plunger assembly 206 is fixedly engaged with the outer shell by engaging the lower tab 182 of the tube support 108 to the indent 134 of the outer shell 102. The engagement area at the indent 134 may be fused or glued to prevent separation of the plunger assembly 206 from the outer shell 102.

To complete the outer shell assembly 208, the lower stop portion 197 of the gauge 110 is positioned within the upper portion 112 of the outer shell 102 with the indicator 201 of the lower stop portion 197 extending visibly through the centrally positioned slot 114. The adjustment ring 199 is then threadably engaged to the threaded upper portion 113 of the outer shell 102, the upper stop portion 198 of the gauge 110 is secured to the lower stop portion 197 of the gauge 110, and the end cap 200 is secured to the upper portion 113 of the outer shell 102 to complete the outer shell assembly 208. A complete assembly of the syringe injection aid 100 finds the side cap 104 pivotably secured to the first and second side portions 139 of the side cap positioner 136.

To use the assembled syringe injection aid 100, a syringe 10, with its safety cap (not shown) in place over the needle 12, is placed within the syringe injection aid 100 such that the body 14 of the syringe 10 is substantially encompassed by the central body portion 180 of the tube support 108. Note that widened opening 122 of the outer shell 102 is configured to accept the side handles 20 of the syringe 10 to accurately position the syringe 10 within the syringe injection aid 100. At this point, the entire syringe 10, including the safety cap covered needle 12 is substantially encompassed by the syringe injection aid 100 and the side cap 104 may be pivoted downward and snapped into a closed position to complete the enclosure of the syringe 10. The upper and lower retention tabs 148 of the side cap press against the body 14 of the syringe 10 helping to maintain the position of the syringe 10.

With the empty syringe 10 loaded into the syringe injection aid 100, the adjustment ring 199 of the gauge 110 may be dialed up or down the threaded upper portion 112 of the outer shell 102 to a desired dosage indication, as indicated by a scale on the syringe injection aid 100 and by the indicator 201 of the lower stop portion 197 of the gauge 110. It should be noted that the components of the syringe injection aid 100 have been designed specific to a standard syringe, for example, a 100 unit B-D™ syringe, and thus the dosage indication on the syringe injection aid 100 has been calibrated such that operation of the syringe injection aid 100 will provide the user with the appropriate dosage. However, various embodiments of a syringe injection aid, as described herein, may be designed for any size/type syringe and the dosage indication may be calibrated accordingly.

Next, the syringe injection aid 100 may be positioned in a vertical orientation such that the end cap 202 is upon a flat surface and the needle safety cap upon the syringe needle 12 is visible to the user at the open end of the syringe injection aid. Upon removing the needle safety cap from the needle 12, the medication vial 15 may be placed upon the needle 12. Note that the tube support insert 196 and the lower stabilizer 152 of the side cap 104 essentially establish a collar configuration that is configured to fit about the neck 17 of the vial 15 and thereby center the vial 15 on the needle 12 as well as prevent over insertion of the needle into the vial. This positioning by the syringe injection aid ensures that the syringe 10 can accurately draw from the vial 15 without introducing air into the syringe 10.

Engagement of the neck 17 of the vial 15 with the syringe injection aid 100 causes engagement with the latch trigger 194 which is pushed up to causing the latch 192 to pivot in toward to the central body portion 180 of the tube support 108. Prior to this, the latch 192 extended outward from the latch slot 130 of the outer shell 102 in an orientation substantially perpendicular to the outer shell 102. In the outward orientation, the latch 192 blocks the syringe-filling pulling movement of the plunger 106 until the neck 17 of the vial 15 has engaged the syringe injection aid 100. Upon engagement, one may hold the syringe injection aid 100 and vial 15 with one hand and easily draw back the plunger 106 by grasping the engagement flange 156 to draw the medication from the vial 15 into the syringe 10. The drawing of the plunger 106 also serves to draw the plunger 22 of the syringe 10 as slotted stop 162 of the plunger 106 engages the plunger cap 23. The plunger 106 is drawn back until the top cap 158 of the plunger 106 contacts the lower stop portion 197 of the gauge 110.

The vial 15 may now be withdrawn from the syringe injection aid 100. With the needle 12 of the syringe 10 still contained within the confines of the syringe injection aid 100, the syringe injection aid 100 may then be positioned flatly against a desired injection site. Once in position, a single hand of the user may hold the syringe injection aid 100 and push the plunger 106 forward at which time the catch 170 of the ratchet 166 engages the slatted, interior back surface 164 of the plunger 106, the ratchet arms 167 engage the side handles 20 to propel the syringe body 14 forward, and slotted stop 162 of the plunger 106, which is already engaged with the plunger cap 23 of the syringe 10, may propel the plunger 22 of the syringe 10 forward.

The engagement of the ratchet arms 167 with the side handles 20 of the syringe 10 pushes the syringe body 14 forward for the length of the needle 12 of the syringe 10 as the ratchet body 168 slides along upper tab 178 of the tube support 108 until the ratchet body 166 contacts the central body portion 180 of the tube support 108. At this point, the upper tab 178 of the tube support 108 contacts the catch 170 of the ratchet 166 causing the ratchet 166 to disengage from the slatted, interior back surface 164 of the plunger 106. Any further forward movement by the ratchet 166 is stopped upon the ratchet 166 contacting the central body portion 180 of the tube support 108 which also stops any further forward movement of the syringe body 14, thus establishing an injection depth for the syringe needle 12. However, the plunger 106 continues forward pushing the plunger 22 of the syringe 10 forward to deliver the medication within the syringe 10 and complete the injection. As such, the syringe injection aid 100 operates to control the depth of penetration of the needle 12 while substantially simultaneously delivering the desired dosage of medication.

After completion of the injection, the needle safety cap may be placed over the syringe needle 12 and used to push the syringe 10 inward until the entire syringe 10 is once again within the confines of the syringe injection aid 100. Pushing the syringe 10 inward results in movement of the plunger 106 whereby the latch 192 is caused to pivot outward thereby locking the syringe injection aid 100 until another use of the syringe injection aid 100 is desired. Notably, throughout the placement of the syringe 10 within the syringe injection aid 100, the loading of the syringe 10 with medication, the delivery of the injection, and the withdrawal of the needle 12, the needle 12 may be kept within the confines of the syringe injection aid 100 preventing erroneous jabs or contamination of the needle 12. Further, with the syringe injection aid 100 in the locked position, a user may draw the side cap 104 upward and remove the syringe 10 and put a new syringe 10 in place within the syringe injection aid readying it for another use.

Figure 5:
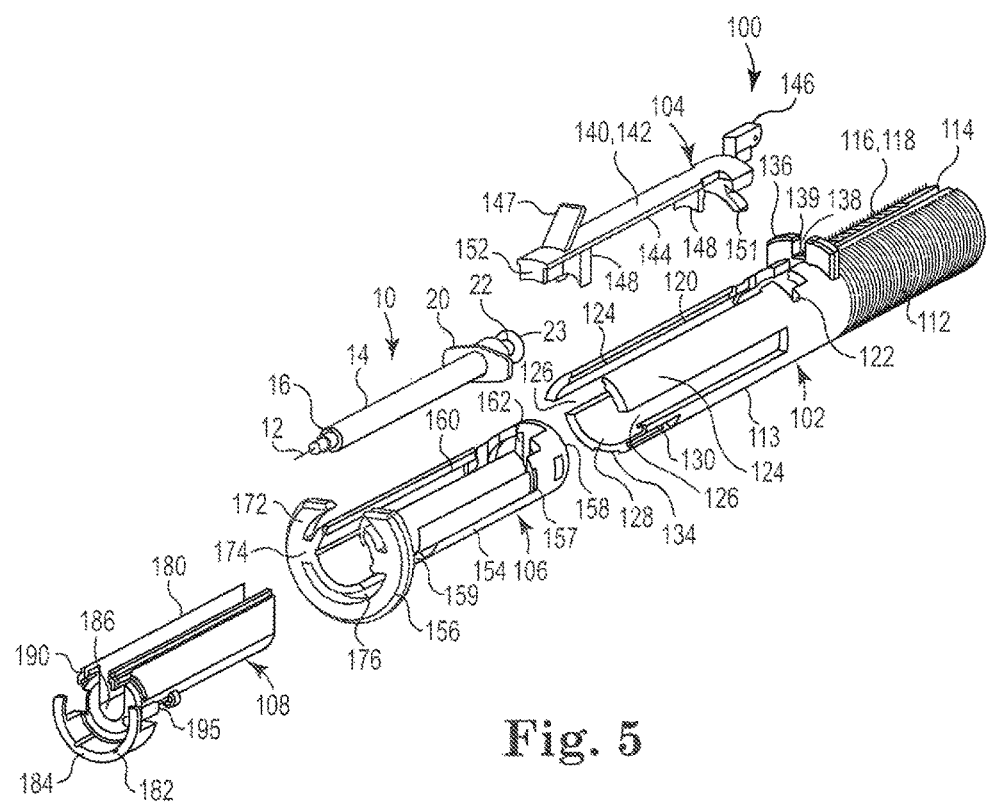
FIG. 5 is an exploded assembly view of a syringe injection according to various embodiments.

In an alternative embodiment, see FIG. 5, the ratchet 166 may be eliminated which also eliminates the need for the slatted interior surface rear surface 164 of the interior of the plunger 106. Further, the upper tab 178 of the tube support 108, whose purpose is to engage the ratchet 166, may also be eliminated. Further, the ratchet stop 150 of the side cap 104 has been replaced with arms 151 that rest behind, i.e. towards the syringe plunger 22, the side handles 20 of the syringe. Note that the tube support insert 196, latch trigger 194, spring, and latch 192 as well as gauge 110 are not shown in the illustration of FIG. 5, but should still be considered elements of the embodiment. In this configuration, the syringe plunger 22, which is engaged with the plunger 106, is used to move the body 14 of the syringe 10 forward, towards the injection site rather than the ratchet 166. The tube support 108 acts as a stop to the side handles 20 of the body 14 of the syringe 10 to prevent further forward movement of the body 14, which also serves to set the depth of needle 12 penetration at the injection site.

Further alternative embodiments are illustrated in FIGS. 6A-B, where FIG. 6A illustrates an exploded view of a syringe injection aid and FIG. 6B illustrates a substantially assembled syringe injection aid of FIG. 6A relative to a syringe. Here again, the ratchet 166 may be eliminated which also eliminates the need for the slatted interior surface rear surface 164 of the interior of the plunger 106. Further, the upper tab 178 of the tube support 108, whose purpose is to engage the ratchet 166, may also be eliminated. It is replaced by tab 602 having an arcuate shape for engaging curved receiving slot 176. Further, the ratchet stop 150 of the side cap 104 has been removed. Side cap 104 instead includes a slot 604 through the side cap 104 that is configured to fit a syringe retainer button 606. Syringe retainer button 606 includes an extended portion 608. The raised positioning tab 146 of FIG. 1 is replaced with a dual-armed positioning tab 610 that is configured to receive the extended portion 608 between the arms. The syringe retainer button 606 rests against a syringe 10, i.e. towards the syringe plunger 22, the side handles 20 of the syringe, to retain and immobilize the body of the syringe 10 with respect to the syringe injection aid 100. Note that the gauge 110 is not shown in the illustrations of FIGS. 6A-B, but should still be considered elements of the embodiment. Also, reference numerals for parts consistent with those labeled in FIGS. 1-4 are not repeated but should be considered the same or similar as shown in those figures. In this configuration, the syringe plunger 22, which is engaged with the plunger 106, is used to move the body 14 of the syringe 10 forward, towards the injection site rather than the ratchet 166. The tube support 108 acts as a stop to the side handles 20 of the body 14 of the syringe 10 to prevent further forward movement of the body 14, which also serves to set the depth of needle 12 penetration at the injection site.

Figure 7A:
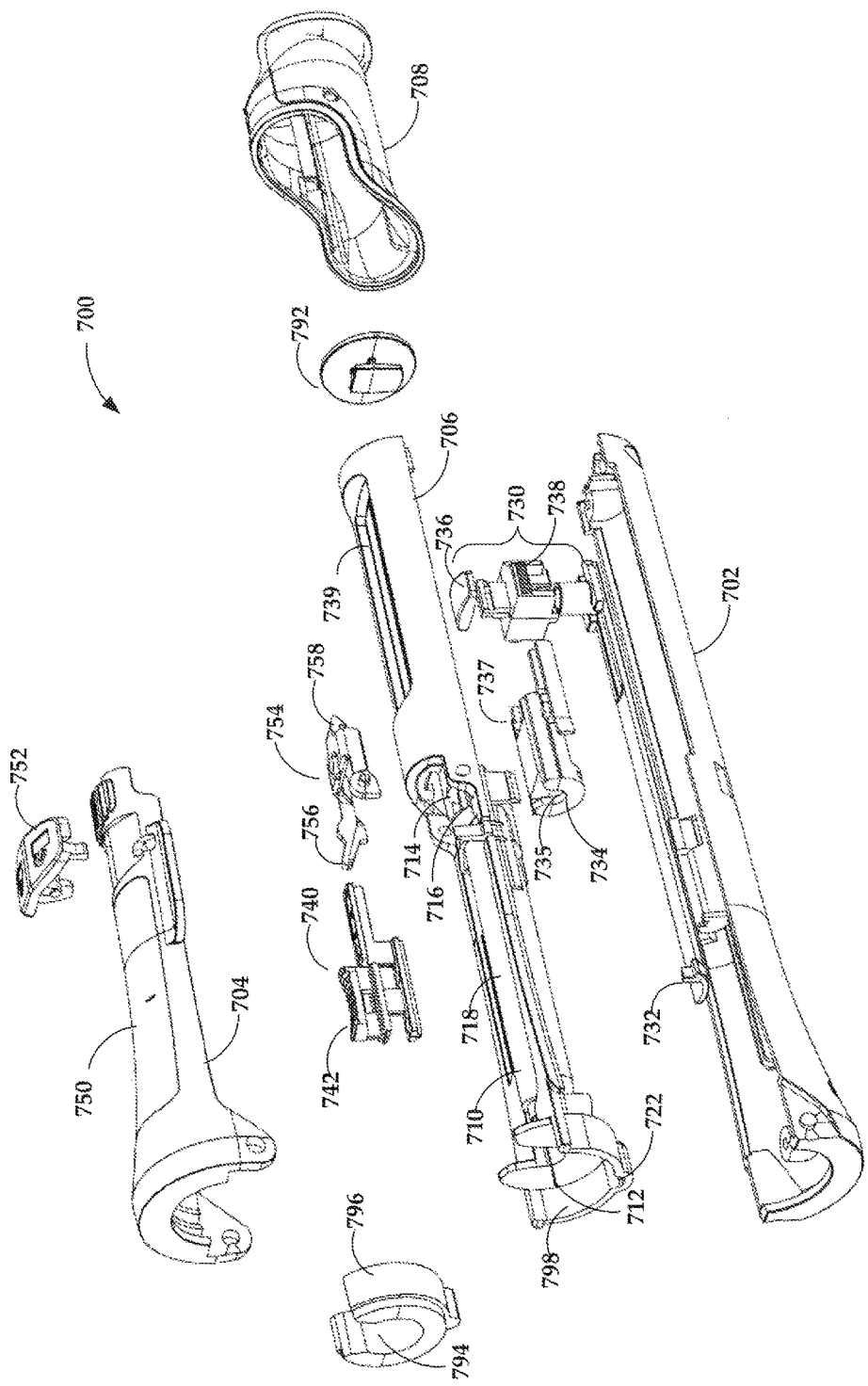
FIG. 7A is an exploded assembly view of a syringe injection aid according to various embodiments.

Further alternative embodiments are illustrated in FIGS. 7A-D, where FIG. 7A illustrates an exploded view of a syringe injection aid 700. The syringe injection aid 700 has an outer shell comprising a lower portion 702, an upper portion 706, and a cover 704, which collectively form the body of the syringe injection device. In addition, the syringe injection aid includes a plunger control grip 708, which is slidably coupled to the assembled upper 706 and lower 702 portions of the outer shell. The body can take any variety of shapes including a tubular shape, as shown, and includes an opening at a first end 722. The cover 704 pivotably attaches to the body. For example, the cover 704 can pivotably attach to the lower portion of the outer shell 702 at the first end 722. Alternatively, the cover 704 can pivotably attach to any other location on the body, e.g., lengthwise along the lower portion of the outer shell 702 or to the top portion of the outer shell 706. The cover 704 could also slidably couple to the upper 706 and/or lower 702 portions of the outer shell. The cover 704 includes a transparent portion 750, which operates as a window into the syringe injection aid. The transparent portion 750 can be any shape and size, but it allows a user to see into the device, and specifically, to see a syringe 710 enclosed within the syringe injection device.

As discussed above, the syringe injection aid 700 is configured to hold and/or encase a syringe 710 in a cavity 720. The cover 704, when in an open position, exposes the cavity 720 and/or a syringe 710. The syringe 710 includes a body 718, needle 712, plunger 716, and a plunger cap 714. The transparent portion 750 of the cover 704 allows a user to see the volume/dosage markings printed on the syringe. The syringe injection aid 700 includes a volume control mechanism 730. The volume control mechanism 730 includes a button arrangement 736 that is slidably coupled with the device body. For example, the button arrangement 736 extends outward from the body through an aperture 739 in the upper portion of the outer shell 706 and moves along the length of the body through the aperture 739. While the exposed portion of the button arrangement 736 can take a variety of shapes and sizes, as can the aperture 739, in certain embodiments the button arrangement 736 is pressed to release a toothed portion 738 to enable movement of an indicator 732. The toothed portion 738 can be located on one or both sides of the volume control mechanism 730 to increase the security/locking of the button 736/indicator 732 in place. The button arrangement 736 can also be configured in a variety of designs including a double-button squeezable control for indicator 732. The volume control mechanism 730 is configured to allow a user to manipulate the button arrangement 736 to move the indicator 732 and set the volume with which the syringe 710 will be filled. The button arrangement 736 locks into place with the toothed portion 738 and operates as a stop for the syringe plunger 716. The coupling between the indicator 732 and button 736 is configured to facilitate use of the syringe volume markings and can be adjusted for different sized syringes, if necessary. Thus, the indicator 732 is also visible through the transparent portion 750 of the cover 704. This provides for direct alignment and use of the syringe volume markings when filling the syringe 710. However, as discussed above, the syringe injection aid may also include a calibrated scale/gauge to facilitate syringe volume control.

The syringe is filled, and emptied, by moving the plunger control grip 708 along the length of the body. The plunger control grip 708 couples to the outside of the body by encircling, or partially encircling, at least a portion of the body's circumference. As shown, the plunger control grip 708 can be ergonomically designed for gripping with one hand while encircling the circumference of the device body. However, the plunger control grip 708 can be configured in a variety of shapes and sizes. The plunger control grip 708 couples to a plunger control 734 located within the device body. The plunger control 734 includes a cavity 735 configured to receive the syringe plunger cap 714. When the plunger control grip 708 is slid backward (i.e., away from the first end of the body 722) the plunger 716 is extended away from the syringe body 718 to fill the syringe 710. Similarly, when the plunger control grip 708 is slid forward (i.e., toward the first end of the body 722), the plunger 716 is returned to the syringe body 718 to empty the syringe 710. Also coupled to the upper portion of the outer shell 706 is a plunger locking mechanism 754. The plunger locking mechanism can be pivotably coupled to the upper portion of the outer shell 706 or another portion of the device body. When the cover 704 is open, the plunger locking mechanism 754 prevents the plunger control 734 from moving in a backward direction via a hook 758 coupled to a lip 737, or other portion on the plunger control 736 configured to secure to the hook 758. When the cover 704 is closed, e.g., secured to the body, the cover 704 pushes down on lever 756 to lift and release hook 758. This allows a syringe 710 to be filled after being securely placed in the syringe injection aid 700 without inadvertently pre-filling the syringe 710 with air, or other material. The lever 756 can also help secure the syringe 710 in place during filling.

In addition to control of the syringe plunger 716, the syringe injection aid 700 also controls movement of the syringe 710. Coupled to the cover 704 is a locking mechanism 752. Locking mechanism 752 prevents forward motion of the syringe 710 when in a locked position and allows forward motion of the syringe 710 when in an unlocked position. This may be implemented in a number of ways including with a rocker switch that inserts a barrier between the syringe (e.g., one or more of the syringe side handles) and the first end of the body 722. When positioned adjacent, or substantially adjacent the one or more side handles, the locking mechanism 752 prevents the syringe needle 712 from extending beyond the first end of the body 722 when in a locked position. Moving the locking mechanism 752 to the unlocked position therefore removes the barrier and allows the syringe 710, and needle 722, to move forward beyond the first end 722 and into the subject being injected (e.g., soft tissue). The syringe injection aid 700 further includes a needle depth control mechanism 740 to control how far into the subject the needle 712 is inserted. The needle depth control mechanism 740 is positioned along the length of the body, in the cavity 720 exposed by the cover 704. It is calibrated, at any variety of lengths, to control the distance that the needle 712 extends outward from the syringe injection aid 700, and thus the depth the needle is injected into a subject. The needle depth control mechanism 740 is manually controlled 742 by sliding the mechanism forward or backward and includes an indicator to signify the selected needle depth. This also facilitates the use of a variety of sizes of needles (e.g., ½" and/or 5/16" in length).

The syringe injection aid 700 can also accommodate a variety of sizes of medicament vials. A vial receiving insert 796 can be positioned in a cavity 798 at the first end 722. The vial receiving insert 796 includes an aperture 794 with a diameter sized to receive the neck and/or cap of a medicament vial. The insert 794 can be made of a variety of materials such as rubber or foam for easy insertion and removal from the first end 722. The material also helps to grip and hold the vial to the syringe injection aid 700 during the filling process. Depending on the size of the medicament vial neck and/or cap, an insert with a corresponding aperture of diameter is selected and inserted into the first end 722 (and replaced with another insert when a different sized vial is used). The opposing end of the syringe injection aid 700 can include an end cap 792. The end cap 792 can be configured to stabilize the syringe injection aid when it is in a vertical position and resting on a surface on the end cap 792. For example, the end cap 792 can be flat or slightly rounded to facilitate inserting a medicament vial into the first end 722 of the syringe injection aid 700. Alternatively, the end cap 792 could be flared, similar to the shape of the first end 722, or take any other shape. The end cap can also be of a variety of materials including non-slip materials such as rubber or plastic. Further, the end cap, or other portion of the outer shell, can include an aperture to receive and hold a protective needle cover during an injection process. The syringe injection aid 700 can be manufactured with a variety of materials and combinations therefore, including metal, plastic, and injection molded parts.

Figure 7B:
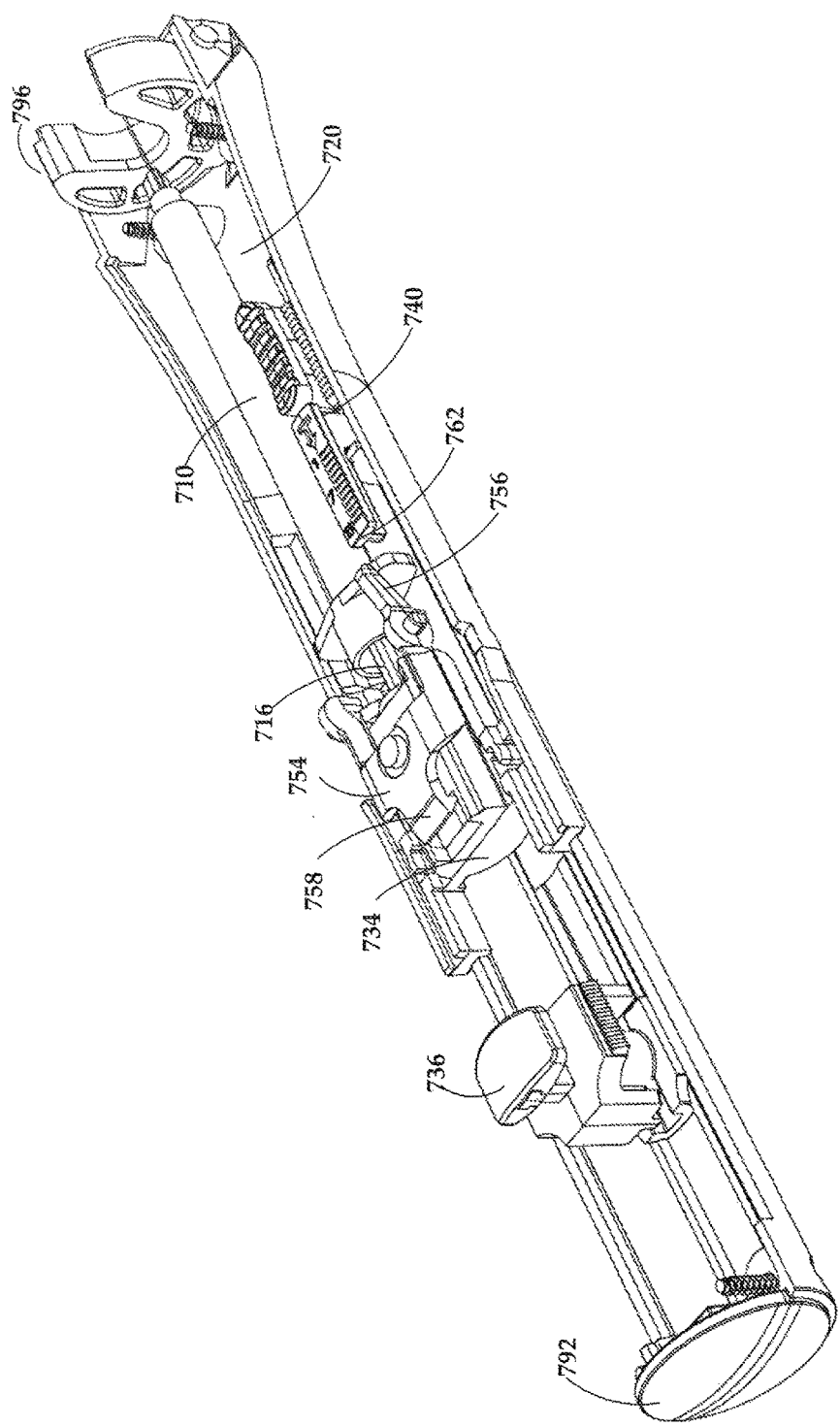
FIG. 7B is a perspective view of the assembled syringe injection aid of FIG. 7A with the top portion of the outer shell removed according to various embodiments.
Figures 7C, 7D:
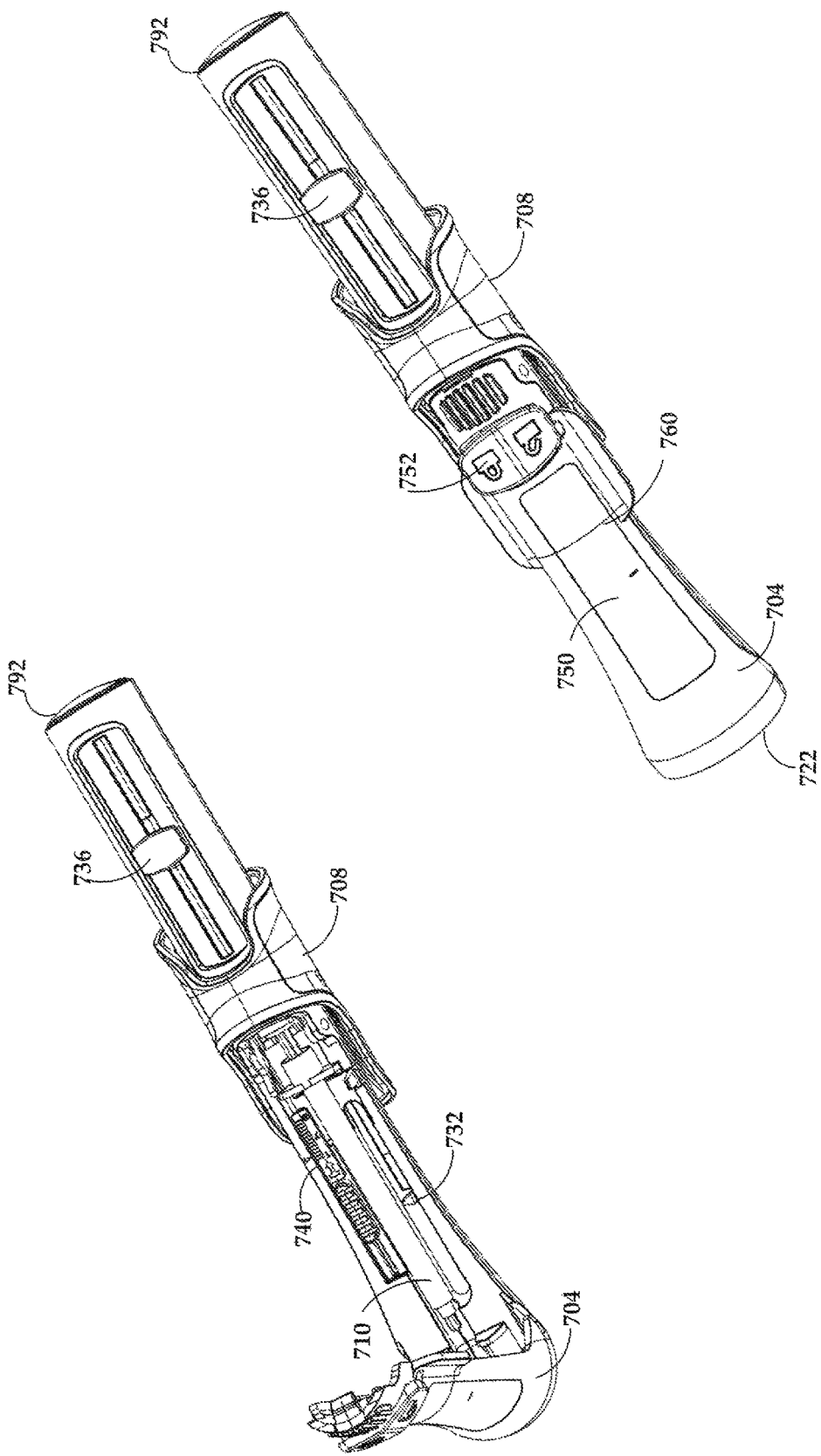
FIG. 7C is a substantially assembled syringe injection aid of FIG. 7A with the cover open according to various embodiments.
FIG. 7D is a substantially assembled syringe injection aid of FIG. 7A according to various embodiments.

FIGS. 7B-D illustrate various perspective views of the syringe injection aid 700 at various levels of assembly. For example, FIG. 7B provides a perspective view of the syringe injection aid 700 without the upper portion of the outer shell 706 or the cover 704. The cavity 720 configured to receive the syringe is shown without additional elements; however, the cavity can be filled with material to more specifically position the syringe 710. It can also be seen how the button arrangement 736 acts as a stop for the plunger control 734 when the toothed portion 738 is locked into a selected position corresponding to the selected fill volume. FIG. 7B also illustrates how end 762 of the needle depth control mechanism 740 prevents the syringe (via at least one side handle) from emerging too far out of the syringe injection aid 700 to control the depth of injection. The further the needle is to be injected into a subject, the closer end 762 is positioned to the open/first end of the body 722. FIG. 7C is a perspective view of the assembled syringe injection aid 700 with a syringe 710 inserted and the cover 704 open. The alignment and positioning of both the volume indicator 732 and the needle depth control mechanism 740 are shown with respect to the syringe 710. FIG. 7D is a perspective view of the assembled syringe injection aid 700 with the cover 704 closed. To facilitate reading the volume markings on the syringe and/or to see the volume indicator 732, the syringe injection aid 700 can optionally include a magnifying device 760. Here, the magnifier 760 can slide along the length of the cover 704 to magnify at least a portion of the syringe volume markings.

The syringe injection aid 700, as described above, is used to hold a syringe 710 to facilitate both filling the syringe 710 and performing an injection with the syringe 710. To do this, the cover 704 is opened and a syringe 710 is placed in the cavity 720 with the syringe plunger 714 positioned in the cavity 735 of the plunger control 734. The needle depth control mechanism 740 is selected, if it is not already set. At this time, the hook 758 prevents the plunger control 734 from moving in a backward (i.e., away from the open end) direction and filling the syringe with air. The cover 704 is then closed. The button arrangement 736 is positioned using the indicator 732 (and optionally a magnifier 760) to select the volume (e.g., dose) for injection. Closing the cover 704 releases the hook 758, and the locking mechanism is pressed to the locked position to secure the syringe body 718 in place so that the syringe plunger 716 will be mobile. If the needle is covered with a protective cap, it can be removed by reaching in through the opening in the first end of the body 722. The medicament vial is then inserted into the first end 722 and held in place by the vial receiving insert 796. The needle 712 is positioned within the syringe injection aid 700 in connection with the vial receiving insert 796 so as to extend minimally into the vial. When the syringe injection aid 700 is positioned substantially vertically (e.g., supported by the end cap 792) the minimal extension of the needle 712 facilitates maximum use of the medication (very little is wasted by being left in the vial) as well as minimal, or no likelihood, of the introduction of air into the syringe. With the syringe needle 712 inserted into the vial, the plunger grip control 708 is moved in a backward direction (i.e., away from the vial) until it is prevented from further movement by the volume control arrangement 730, and more particularly, the button arrangement 736. With the syringe filled with the selected volume, the vial can be removed from the syringe injection aid 700.

Next, the medication can be injected. The needle is still contained within the syringe injection aid 700, so the first end of the body 722 can be placed on, e.g., flush with, the injection site. The locking mechanism is switched to the unlock position. When ready, the user moves the plunger control grip 708 in a forward motion (i.e., toward the first end of the body 722). This single movement moves both the syringe body forward to the desired needle injection depth and, substantially simultaneously, moves the syringe plunger 716 forward to inject the medication. Since the plunger control grip 708 is manually controlled by the user, and is not automatic, the speed of the injection delivery is controlled by the user. After injection, the plunger grip control is moved backward and the syringe injection aid is removed from the injection site. The syringe needle protective cap can be replaced and the locking mechanism set to again contain the needle 712 within the syringe injection aid 700 until the syringe 710 is removed.

In summary, the syringe injection aid described herein is an ergonomically designed tool to facilitate both filling syringes and performing injections. The device is especially helpful for those needing to perform injections on themselves, and those that have coordination and/or visual impediments that hinder the ability to use typically sized syringes.

Systems, devices or methods disclosed herein may include one or more of the features structures, methods, or combination thereof described herein. For example, a device or method may be implemented to include one or more of the features and/or processes above. It is intended that such device or method need not include all of the features and/or processes described herein, but may be implemented to include selected features and/or processes that provide useful structures and/or functionality. For example, the disclosed embodiments may be used for both human and veterinary purposes.

Various modifications and additions can be made to the disclosed embodiments discussed above. Accordingly, the scope of the present disclosure should not be limited by the particular embodiments described above, but should be defined only by the claims set forth below and equivalents thereof.

What is claimed is:

1. An apparatus comprising:
    a body having an opening at a first end of the body;
    a plunger control grip slidably coupled to a portion of a circumference of the body and configured to couple to a syringe plunger;
    a cover pivotably coupled to the first end of the body, wherein in an open position the cover exposes a cavity configured to receive a syringe; and
    a locking mechanism pivotally secured to the cover, wherein the locking mechanism is configured to prevent forward movement of the plunger control grip when in a locked position and to enable forward movement of the plunger control grip when in an unlocked position, wherein the unlocked position is activated by external contact with the locking mechanism and forward movement is in the direction toward the first end of the body.

2. The apparatus of claim 1, wherein the body comprises a volume control mechanism.

3. The apparatus of claim 1, wherein the cavity includes a needle depth control mechanism.

4. The apparatus of claim 1, wherein the cover includes a transparent portion configured to visually expose the syringe when present in the cavity.

5. The apparatus of claim 1, further comprising a vial receiving insert within the first end of the body.

6. The apparatus of claim 1, wherein the body flares outward at the first end.

7. The apparatus of claim 1, wherein the plunger control grip is manually moved along a length of the body.

8. The apparatus of claim 7, wherein the plunger control grip is moved in forward and backward directions along the length of the body.

9. An apparatus comprising:
   a tubular body having an opening at a first end of the tubular body;
   a plunger control grip slidably coupled to and encircling a portion of a circumference of the tubular body and configured to couple to a syringe plunger;
   a cover pivotably coupled to the tubular body, wherein in an open position the cover exposes a cavity configured to receive a syringe; and
   a locking mechanism pivotally secured to the cover, wherein the locking mechanism is configured to prevent forward movement of the plunger control grip when in a locked position and to enable forward movement of the plunger control grip when in an unlocked position, wherein forward movement is in the direction toward the first end of the tubular body.

10. The apparatus of claim 9, wherein the locking mechanism is a rocker mechanism.

11. The apparatus of claim 9, wherein the tubular body comprises a volume control mechanism.

12. The apparatus of claim 9, wherein the cavity includes a needle depth control mechanism.

13. The apparatus of claim 9, wherein the cover includes a transparent portion configured to visually expose the syringe when present in the cavity.

14. The apparatus of claim 9, wherein the tubular body flares outward at the first end.

15. An apparatus comprising:
   a body having an opening at a first end of the body and the body being configured to receive and substantially confine a syringe having a syringe plunger, a syringe body, and a needle;
   a plunger control grip slidably coupled to a portion of a circumference of the body and configured to couple to the syringe plunger and the syringe body;
   a cover pivotably coupled to the first end of the body, wherein in an open position the cover exposes a cavity configured to receive the syringe; and
   a locking mechanism pivotally secured to the cover, wherein the locking mechanism is configured to prevent forward movement of the plunger control grip when in a locked position and to enable forward movement of the plunger control grip when in an unlocked position, wherein forward movement of the plunger control grip is in the direction toward the first end of the body and engages the syringe body to move the needle a distance beyond the confines of the body.

16. The apparatus of claim 15, wherein moving the plunger control grip away from the first end of the body engages the syringe plunger to fill the syringe.

17. The apparatus of claim 15, wherein the plunger control grip is manually moved along a length of the body.

18. The apparatus of claim 15, wherein the body comprises a volume control mechanism.

19. The apparatus of claim 15, wherein the cavity comprises a needle depth control mechanism.

20. The apparatus of claim 15, further comprising a vial receiving insert within the first end of the body.

* * * * *